United States Patent
Nakai et al.

(10) Patent No.: US 12,167,831 B2
(45) Date of Patent: Dec. 17, 2024

(54) ADHESIVE FOR ENDOSCOPE, CURED PRODUCT, ENDOSCOPE, AND METHOD FOR PRODUCING ENDOSCOPE

(71) Applicant: FUJIFILM Corporation, Tokyo (JP)

(72) Inventors: Yoshihiro Nakai, Ashigarakami-gun (JP); Kazushi Furukawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 893 days.

(21) Appl. No.: 17/110,758

(22) Filed: Dec. 3, 2020

(65) Prior Publication Data

US 2021/0106210 A1  Apr. 15, 2021

Related U.S. Application Data

(63) Continuation of application No. PCT/JP2019/025988, filed on Jun. 28, 2019.

(30) Foreign Application Priority Data

Jul. 10, 2018 (JP) ................. 2018-131087

(51) Int. Cl.
| | | |
|---|---|---|
| A61B 1/00 | (2006.01) | |
| A61B 1/005 | (2006.01) | |
| A61B 1/05 | (2006.01) | |
| C08G 59/22 | (2006.01) | |
| C08G 59/38 | (2006.01) | |
| C08G 59/50 | (2006.01) | |
| C08K 5/1515 | (2006.01) | |
| C08K 5/17 | (2006.01) | |
| C09J 163/00 | (2006.01) | |
| C09J 163/04 | (2006.01) | |
| G02B 23/24 | (2006.01) | |

(52) U.S. Cl.
CPC ........ *A61B 1/00071* (2013.01); *A61B 1/0011* (2013.01); *A61B 1/0055* (2013.01); *C08G 59/226* (2013.01); *C08G 59/38* (2013.01); *C08G 59/5006* (2013.01); *C08G 59/5013* (2013.01); *C08G 59/504* (2013.01); *C08K 5/1515* (2013.01); *C08K 5/17* (2013.01); *C09J 163/00* (2013.01); *C09J 163/04* (2013.01); *A61B 1/00096* (2013.01); *A61B 1/051* (2013.01); *C08G 2650/50* (2013.01); *G02B 23/2476* (2013.01)

(58) Field of Classification Search
CPC . A61B 1/00071; A61B 1/0055; A61B 1/0011; A61B 1/051; A61B 1/00096; C08G 59/226; C08G 59/504; C08G 59/38; C08G 59/5006; C08G 59/5013; C08G 2650/50; C08K 5/1515; C08K 5/17; C09J 163/04; C09J 163/00; G02B 23/2476
See application file for complete search history.

(56) References Cited

U.S. PATENT DOCUMENTS

| | | |
|---|---|---|
| 2011/0245614 A1 | 10/2011 | Nakamura |
| 2016/0088998 A1 | 3/2016 | Nagai et al. |
| 2016/0222261 A1 | 8/2016 | Yokoyama et al. |
| 2019/0082937 A1 | 3/2019 | Hayashi et al. |
| 2020/0187755 A1 | 6/2020 | Furukawa et al. |

FOREIGN PATENT DOCUMENTS

| | | | |
|---|---|---|---|
| CN | 105455764 A | | 4/2016 |
| CN | 106220829 | * | 12/2016 |
| CN | 106220829 A | * | 12/2016 |
| EP | 2295487 | * | 3/2011 |
| EP | 3 281 965 A1 | | 2/2018 |
| JP | 2002-238834 A | | 8/2002 |
| JP | 2005-152461 A | | 6/2005 |
| JP | 2008-284191 A | | 11/2008 |
| JP | 2017-214546 A | | 12/2017 |
| JP | 2018-90651 A | | 6/2018 |
| WO | WO 2112/021258 | * | 2/2012 |
| WO | 2015/093127 A1 | | 6/2015 |
| WO | 2016/159224 A1 | | 10/2016 |
| WO | 2019/044755 A1 | | 3/2019 |

OTHER PUBLICATIONS

The machine English translation of CN 106220829, Zhang, Dec. 14, 2016.*
International Search Report issued Sep. 17, 2019 in International Application No. PCT/JP2019/025988.
International Preliminary Report on Patentability issued Nov. 3, 2020 in International Application No. PCT/JP2019/025988.
Extended European Search Report dated Aug. 19, 2021, issued by the European Patent Office in corresponding application No. 19834399.8.
Office Action issued Sep. 1, 2023 in Chinese Application No. 201980033606.6.

* cited by examiner

*Primary Examiner* — Patrick D Niland
(74) *Attorney, Agent, or Firm* — Sughrue Mion, PLLC

(57) ABSTRACT

Provided are an adhesive for an endoscope, a cured product of the adhesive for an endoscope, an endoscope produced using the adhesive for an endoscope, and a method for producing an endoscope. The adhesive for an endoscope includes at least one epoxy resin (A) selected from the group consisting of bisphenol A epoxy resins, bisphenol F epoxy resins, and phenol novolac epoxy resins, a polyamine compound (B), and a specific compound (C) having an epoxy group.

5 Claims, 3 Drawing Sheets

ADHESIVE FOR ENDOSCOPE, CURED PRODUCT, ENDOSCOPE, AND METHOD FOR PRODUCING ENDOSCOPE

CROSS-REFERENCE TO RELATED APPLICATIONS

This application is a Continuation of PCT International Application No. PCT/JP2019/025988 filed on Jun. 28, 2019, which claims priority under 35 U.S.C. § 119 (a) to Japanese Patent Application No. 2018-131087 filed in Japan on Jul. 10, 2018. Each of the above applications is hereby expressly incorporated by reference, in its entirety, into the present application.

BACKGROUND OF THE INVENTION

1. Field of the Invention

The present invention relates to an adhesive for an endoscope, a cured product, an endoscope, and a method for producing an endoscope.

2. Description of the Related Art

Endoscopes for examining human body cavities are repeatedly used. Thus, a flexible tube constituting an insertion section of an endoscope needs to be washed and disinfected with chemicals after each use.

In particular, when an endoscope is inserted into a highly susceptible region, such as a bronchus, high cleanliness at the level of sterilization higher than disinfection is required. Accordingly, the use of not only an ethylene oxide gas (EOG) sterilization treatment, which is widely practiced, but also treatments having higher sterilization effects (e.g., hydrogen peroxide plasma treatment) has been demanded.

The insertion section of an endoscope is inserted into a body cavity through the oral cavity or nasal cavity. To alleviate foreign body sensation and pain in patients during the insertion, the insertion section of an endoscope desirably has a smaller diameter. Thus, instead of bulky members such as screws, adhesives are mainly used to bond together members constituting the insertion section.

Among the adhesives, epoxy adhesives, which have high workability and also have high adhesiveness after being cured and then subjected to a sterilization treatment, that is, have high sterilization resistance, are used for endoscopes. For example, JP2008-284191A discloses an epoxy adhesive including a base adhesive and 1 wt % or more and 30 wt % or less of a multiwalled carbon nanotube mixed with the base adhesive, the base adhesive being composed of at least one resin (base resin) selected from the group consisting of bisphenol A epoxy resins and bisphenol F epoxy resins and a polyamidoamine curing agent, the multiwalled carbon nanotube having a diameter of 350 nm or less. JP2008-284191A states that this adhesive has high sterilization resistance.

SUMMARY OF THE INVENTION

When the curing temperature of an epoxy adhesive is high during a process for producing an endoscope, the endoscope will be exposed to high temperature for many times during the production process, and thus the curing temperature needs to be as low as possible. That is, an epoxy adhesive used for an endoscope is required to have low-temperature curability.

In a treatment using an endoscope, an insertion section of the endoscope is inserted into a body cavity, an observation target such as the inner wall of an organ or an affected area such as a tumor (hereinafter, the observation target and the affected area are collectively referred to as the "affected area or the like") is photographed to obtain information of the affected area or the like, and, if necessary, the affected area is, for example, resected with a treatment tool, such as forceps or an injection needle, put out of a forceps port disposed at a tip portion of the insertion section. To smoothly and reliably deliver the insertion section of the endoscope to the affected area or the like and obtain detailed information on the affected area or to perform a highly accurate treatment using the endoscope, it is necessary to increase the flexibility with respect to bending (bending resistance) of the insertion section to improve operability.

However, adhesives of the related art including the adhesive disclosed in JP2008-284191A have insufficient low-temperature curability, and cured products thereof (adhesive cured products) have insufficient flexibility. When an insertion section of an endoscope to which such an adhesive is applied is bent to a high curvature, the adhesive cured product tends to crack or break.

To provide an adhesive for an endoscope with sufficient low-temperature curability and an adhesive cured product with sufficient flexibility, the present inventors investigated the use of a plasticizer. As a result, sufficient low-temperature curability of an adhesive for an endoscope and sufficient flexibility of an adhesive cured product were achieved. However, when an endoscope in which the plasticizer was added and incorporated into the adhesive for an endoscope was used for a long period of time, the following problems arose: the plasticizer bled out, and as a result, the adhesive cured product became opaque; and the amount of the plasticizer in the cured product decreased, and as a result, mechanical properties such as flexibility changed. Furthermore, it was found that the adhesive cured product in the endoscope was likely to degrade when repeatedly subjected to a sterilization treatment.

An object of the present invention is to provide an adhesive for an endoscope and a cured product thereof. The adhesive for an endoscope exhibits a high curing reaction rate even at low temperature. In a state where an endoscope-constituting member is fixed with the cured product obtained by curing reaction, the cured product has high flexibility. In addition, even after a long-term use in the fixed state, the transparency of the cured product can be sufficiently maintained. Furthermore, the cured product is less likely to degrade if repeatedly subjected to a sterilization treatment in the above fixed state. Another object of the present invention to provide an endoscope that includes an endoscope-constituting member fixed with the cured product, that can sufficiently maintain the fixed state if subjected to bending, that can sufficiently maintain the transparency of the cured product even after a long-term use, and that is less likely to experience a decrease in performance even after repetition of sterilization treatments. Still another object of the present invention to provide a method for producing the endoscope by using the adhesive for an endoscope.

The present inventors have conducted intensive studies and discovered that an adhesive for an endoscope, the adhesive containing a specific epoxy resin, a polyamine compound, and a compound having a specific structure having an epoxy group, is cured at a high curing reaction rate even at low temperature, that a cured product obtained by curing reaction has high flexibility, that oozing of components out of the cured product can be suppressed over a long period of time to sufficiently maintain the transparency of the cured product, and that the cured product is less likely to degrade if repeatedly subjected to a sterilization treatment. The present invention has been accomplished by performing further investigations on the basis of the above findings.

The above objects have been achieved by the following means.

<1>

An adhesive for an endoscope includes at least one epoxy resin (A) selected from the group consisting of bisphenol A epoxy resins, bisphenol F epoxy resins, and phenol novolac epoxy resins, a polyamine compound (B), and a compound (C) represented by general formula (1) below.

$$R \text{—} \left( \text{—} \underset{}{\triangleleft} \text{O} \right)_n \quad \text{general formula (1)}$$

In the formula, n represents an integer of 1 to 6. R represents an aliphatic hydrocarbon group, an alicyclic hydrocarbon group, an aromatic hydrocarbon group, an aromatic heterocyclic group, or a combination thereof, the groups and the combination each having a valence of n. R does not adopt a -phenylene-methylene-phenylene-structure or bind to an epoxy group in the formula to form a ring.

<2>

In the adhesive for an endoscope according to <1>, the polyamine compound (B) is a primary polyamine compound.

<3>

In the adhesive for an endoscope according to <1> or <2>, R is an aliphatic hydrocarbon group, an alicyclic hydrocarbon group, an aromatic hydrocarbon group, or a combination thereof.

<4>

In the adhesive for an endoscope according to any one of <1> to <3>, n is an integer of 2 to 4.

<5>

In the adhesive for an endoscope according to <4>, n is 2 or 3.

<6>

In the adhesive for an endoscope according to <5>, n is 2.

<7>

A cured product is formed by curing the adhesive for an endoscope according to any one of <1> to <6>.

<8>

An endoscope includes the cured product according to <7> and a member fixed with the cured product.

<9>

A method for producing an endoscope includes fixing a member by using the adhesive for an endoscope according to any one of <1> to <6>.

In the description of the present invention, "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

The adhesive for an endoscope according to the present invention exhibits a high curing reaction rate even at low temperature. In an endoscope in which a member is fixed with a cured product of the adhesive, the cured product has high flexibility. Furthermore, the cured product can sufficiently maintain transparency if the endoscope is used for a long period of time. Furthermore, the cured product is less likely to degrade if the endoscope is repeatedly subjected to a sterilization treatment, and the fixed state of the member can be maintained over a long period of time. The cured product according to the present invention has high flexibility, can maintain sufficient transparency if exposed to a high-temperature and high-humidity environment for a long period of time, and is less likely to degrade if repeatedly subjected to a sterilization treatment. Therefore, the endoscope according to the present invention in which an endoscope-constituting member is fixed with the cured product can sufficiently maintain the fixed state if subjected to bending, can maintain sufficient transparency of the cured product if exposed to a high-temperature and high-humidity environment for a long period of time, and, furthermore, is less likely to undergo degradation in performance if repeatedly subjected to a sterilization treatment. According to the method for producing an endoscope according to the present invention, the above excellent endoscope can be produced.

DESCRIPTION OF THE PREFERRED EMBODIMENTS

Adhesive for Endoscope

Figure 1:
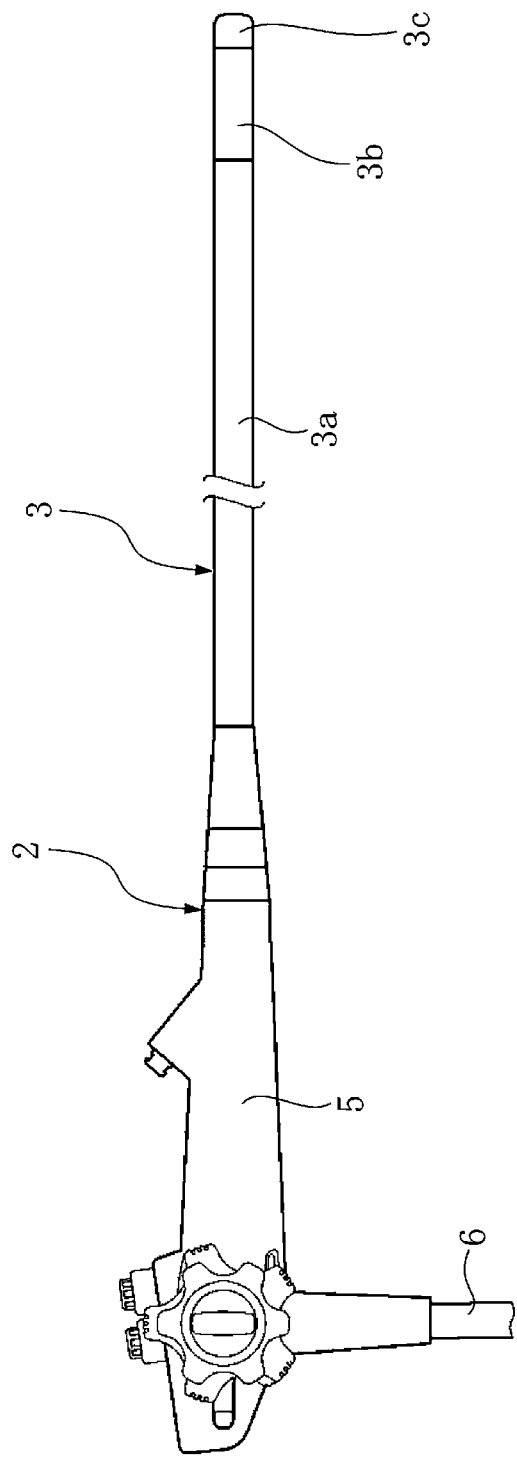
FIG. 1 is an external view illustrating a configuration of an endoscope according to an embodiment of the present invention.

An adhesive for an endoscope includes at least one epoxy resin (A) (hereinafter also referred to as the "component (A)") selected from the group consisting of bisphenol A epoxy resins, bisphenol F epoxy resins, and phenol novolac epoxy resins, a polyamine compound (B) (hereinafter also referred to as the "component (B)"), and a compound (C) (hereinafter also referred to as the "compound (C)" or the "component (C)") represented by general formula (1) below.

$$R \text{—} \left( \text{—} \underset{}{\triangleleft} \text{O} \right)_n \quad \text{general formula (1)}$$

In the formula, n represents an integer of 1 to 6. R represents an aliphatic hydrocarbon group, an alicyclic hydrocarbon group, an aromatic hydrocarbon group, an aromatic heterocyclic group, or a combination thereof, the groups and the combination each having a valence of n. R does not adopt a -phenylene-methylene-phenylene-structure or bind to an epoxy group in the formula to form a ring. The "-phenylene-methylene-phenylene-structure" may have a substituent (e.g., a methyl group or a hydroxy group).

The adhesive for an endoscope according to the present invention is used to fix at least one member selected from the group consisting of resin members (including rubber members), metal members, and glass members constituting the endoscope. The "fixing" is performed by bonding at least one member selected from the group consisting of resin members, metal members, and glass members to, for example, a supporting member constituting the endoscope. The supporting member may be a tube wall or the like of the endoscope or an immovable member fixed to the tube wall or the like, or may be a member whose relative position in the endoscope can be moved like a tube. In the present invention, the term "fixing" is meant to include filling, that is, sealing a space between the above member and the supporting member incorporated with the above member with an adhesive cured product.

Hereinafter, the "adhesive for an endoscope" may be referred to simply as the "adhesive". A fixing portion or a sealing portion formed of the above adhesive cured product between a member and a member may be referred to as an adhesive joint.

The adhesive according to the present invention can be cured at a high reaction rate at low temperature. A cured product formed by curing the adhesive has high flexibility, remains sufficiently transparent if placed in a high-temperature and high-humidity environment for a long period of time, and is less likely to degrade and can maintain high adhesiveness if repeatedly subjected to a sterilization treatment. Therefore, an endoscope produced using the adhesive according to the present invention is less likely to undergo performance degradation if used for a long period of time and repeatedly subjected to a hydrogen peroxide plasma sterilization treatment. Although still not clear, the reasons for this are presumably as follows.

In the adhesive according to the present invention, the compound (C) interpose between the epoxy resins (A) to form a mixture of the epoxy resins (A) and the compound (C), thus causing a decrease in glass transition temperature. Consequently, the mobility of molecular chains constituting the epoxy resins (A) is increased, and in the adhesive according to the present invention, epoxy groups of the epoxy resins (A) and the compound (C) and amino groups of the polyamine compound (B) undergo a curing reaction at a high reaction rate even at low temperature to provide an adhesive cured product having high flexibility and a high inter-component bonding density. Furthermore, since the compound (C) has an epoxy group, a component derived from the compound (C) is incorporated, as a constituent, into a cured product of the epoxy resins (A) and the polyamine compound (B) with a chemical bond to exhibit plasticizing action and also become less likely to bleed out of the cured product. Because of a combination of these factors, the adhesive according to the present invention produces the above effects.

The adhesive for an endoscope according to the present invention may be in any form as long as the components (A) to (C) are included. Specifically, the adhesive for an endoscope according to the present invention may contain a mixture of the components (A) to (C) (one-component type), or may include the components (A) to (C) with one of the components (A) to (C) being separated from the other components (two-component type). Alternatively, the adhesive for an endoscope according to the present invention may include the components (A) to (C) with the components (A) to (C) being separated from each other (three-component type). Embodiments of types of the adhesive according to the present invention will be described below, but the present invention is not limited thereto.

One-Component Adhesive

When the adhesive for an endoscope according to the present invention is a one-component adhesive, the adhesive is preferably preserved at 0° C. or lower in order to keep the components (A) to (C) stably maintained with no reaction occurring or with reaction sufficiently inhibited.

Two-Component Adhesive

When the adhesive for an endoscope according to the present invention is a two-component adhesive, the adhesive for an endoscope according to the present invention may be used in any of the following forms:

(i) The components (A) and (B) are included separately from the component (C), and the components (A) to (C) are mixed together at the point of use;

(ii) The components (A) and (C) are included separately from the component (B), and the components (A) to (C) are mixed together at the point of use; and (iii) The component (A) is included separately from the components (B) and (C), and the components (A) to (C) are mixed together at the point of use.

In the forms (i) and (iii), the adhesive is preferably preserved at 0° C. or lower in order to keep the components stably maintained. In the form (ii), the adhesive is preferably preserved at 40° C. or lower in order to keep the components stably maintained.

Three-Component Adhesive

The adhesive for an endoscope according to the present invention may be used in the following form: the components (A) to (C) are included separately from each other and mixed together at the point of use. The adhesive for an endoscope according to the present invention of three-component type is preferably preserved at 40° C. or lower.

The adhesive for an endoscope according to the present invention is preferably a two-component adhesive in the form (ii) or a three-component adhesive because it is preservable under milder conditions. More preferably, the adhesive for an endoscope according to the present invention is in the form (ii) because the epoxy resin (A) and the compound (C) are in a mixed state and the adhesive can be readily used as a two-component adhesive. If necessary, the adhesive for an endoscope according to the present invention may be preserved in darkness.

In the adhesive according to the present invention, the polyamine compound (B) is preferably mixed such that the mass thereof in terms of active hydrogen equivalent is 0.1 to 1.5, more preferably 0.3 to 1.0, particularly preferably 0.5 to 1.0, relative to the total epoxy equivalent of the epoxy resin (A) and the compound (C).

In the adhesive according to the present invention, the polyamine compound (B) is preferably mixed in an amount of 10 to 75 parts by mass, more preferably 10 to 50 parts, relative to 100 parts by mass of the epoxy resin (A).

In the adhesive according to the present invention, the compound (C) is preferably mixed in an amount of 5 to 50 parts by mass, more preferably 10 to 45 parts by mass, still more preferably 15 to 40 parts by mass, relative to 100 parts by mass of the epoxy resin (A).

When the adhesive for an endoscope according to the present invention is in a form where one of the components (A) to (C) is separated from the others or the components (A) to (C) are separated from each other, a mixture of the components (A) to (C) is prepared at the point of use so as to satisfy the above preferred contents, and the mixture can be used as an adhesive. For example, when the adhesive for an endoscope according to the present invention is a two-component or three-component adhesive in which the component (C) is separated, if the components (A) to (C) are mixed together at the point of use such that the contents of the components (B) and (C) in the mixture satisfy the above preferred contents, the adhesive is included in the adhesive for an endoscope according to the present invention having the above preferred contents. That is, in the form of a two-component or three-component adhesive, the contents of the components (A) to (C) need not satisfy the above preferred contents in a state where the components are separated from each other, and if the above preferred contents are satisfied after mixing, the adhesive is included in the adhesive for an endoscope according to the present invention having the above preferred contents. An adhesive that satisfies the contents of the components (A) to (C) before mixing is also included in the adhesive for an endoscope according to the present invention having the above preferred contents.

The adhesive for an endoscope according to the present invention may include a solvent, an adhesion improver (e.g., a silane coupling agent), a surfactant, a colorant (e.g., a pigment or a dye), a weathering agent, an antioxidant, a heat stabilizer, a lubricant, an antistatic agent, a whitener, a release agent, a conductive agent, a viscosity regulator, a filler (e.g., silica or calcium carbonate), a thixotropy-imparting agent, a diluent, a curing accelerator (preferably an alcohol compound), and a flame retardant, as long as the advantageous effects of the present invention are not impaired.

Epoxy Resin (A)

The adhesive for an endoscope according to the present invention includes at least one of a bisphenol A epoxy resin, a bisphenol F epoxy resin, or a phenol novolac epoxy resin. These epoxy resins may be used alone or in combination.

The bisphenol A epoxy resin used in the present invention is not particularly limited and may be any bisphenol A epoxy resin commonly used as a base resin of an epoxy adhesive. Specific examples include bisphenol A diglycidyl ethers (e.g., "jER825", "jER828", and "jER834" (trade names) manufactured by Mitsubishi Chemical Corporation) and bisphenol A propoxylate diglycidyl ethers.

The bisphenol F epoxy resin used in the present invention is not particularly limited and may be any bisphenol F epoxy resin commonly used as a base resin of an epoxy adhesive. Specific examples include bisphenol F diglycidyl ethers (e.g., "EPICLON 830" (trade name) manufactured by DIC Corporation) and 4,4'-methylenebis(N,N-diglycidylaniline).

The phenol novolac epoxy resin used in the present invention is not particularly limited and may be any phenol novolac epoxy resin commonly used as a base resin of an epoxy adhesive. Specific examples include product number 406775 manufactured by Sigma-Aldrich.

Polyamine Compound (B)

The adhesive according to the present invention contains at least one polyamine compound (B). The polyamine compound (B) included in the adhesive according to the present invention is a compound having, in one molecule, two or more amino groups having active hydrogen. The polyamine compound (B) preferably has a primary amino group, more preferably has two or more primary amino groups. Still more preferably, the polyamine compound (B) is a primary polyamine compound (polyamine compound in which all amino groups are primary amino groups). In the adhesive according to the present invention, a wide variety of polyamine compounds that exhibit curing action in epoxy adhesives can be used.

The number of amino groups having active hydrogen in one molecule of the polyamine compound (B) is preferably 2 to 10, more preferably 2 to 8, still more preferably 2 to 6, further more preferably 2 to 4, particularly preferably 2 or 3. In particular, at least one selected from the group consisting of diamine compounds and triamine compounds is suitable for use.

The active hydrogen equivalent (equivalent of active hydrogen of amino groups) of the polyamine compound (B) is preferably 10 to 2,000, more preferably 20 to 1,000, still more preferably 30 to 900, further more preferably 40 to 800, yet more preferably 60 to 700, particularly preferably 65 to 600.

The active hydrogen equivalent is a value obtained by dividing the molecular weight of the polyamine compound (B) by the number of moles of active hydrogen of amino groups of the polyamine compound (B) (i.e., a molecular weight of one active hydrogen of an amino group in the polyamine compound).

The molecular weight of the polyamine compound (B) is preferably 100 to 6,000, more preferably 100 to 3,000. When the polyamine compound (B) is a polymer (e.g., when the polyamine compound (B) has a polyoxyalkylene group described below), the molecular weight is a number average molecular weight.

In the polyamine compound (B), two or more amino groups are preferably bonded together through a group selected from the group consisting of aliphatic hydrocarbon groups, alicyclic hydrocarbon groups, aromatic hydrocarbon groups, and heterocyclic groups or a combination thereof. In the polyamine compound (B), two or more amino groups are more preferably bonded together through an aliphatic hydrocarbon group, a cyclic hydrocarbon group, an aromatic hydrocarbon group, or a combination thereof, still more preferably bonded together through an aliphatic hydrocarbon group, a cyclic hydrocarbon group, a combination of an aliphatic hydrocarbon group and a cyclic hydrocarbon group, or a combination of an aliphatic hydrocarbon group and an aromatic hydrocarbon group, further more preferably bonded together through an aliphatic hydrocarbon group, a cyclic hydrocarbon group, or a combination of an aliphatic hydrocarbon group and a cyclic hydrocarbon group, and yet more preferably bonded together through an aliphatic hydrocarbon group. These groups may have a heteroatom such as an oxygen atom, a nitrogen atom, or a sulfur atom (preferably an oxygen atom) between carbon-carbon bonds. The aliphatic hydrocarbon group preferably has an oxygen atom between carbon-carbon bonds.

In particular, to provide a cured product with higher flexibility and stronger physical properties, the polyamine compound (B) preferably has, in its molecule, a linear alkylene group or a polyoxyalkylene group, more preferably a polyoxyalkylene group.

The polyamine compound (B) having a linear alkylene group is preferably an alkylenediamine compound, and the polyamine compound (B) having a polyoxyalkylene group is more preferably a polyoxyalkylenediamine compound or a polyoxyalkylenetriamine compound.

The above linear alkylene group may be linear or branched, and the number of carbon atoms in the linear alkylene group is preferably 1 to 20, more preferably 5 to 12. Specific examples of alkylene groups methylene, ethylene, hexamethylene, 2,4,4-trimethylhexamethylene, 2-methylpentamethylene, and dodecamethylene.

The alkylene group in the above polyoxyalkylene group may be a linear alkylene group or a branched alkylene group. The number of carbon atoms in the alkylene group in the above polyoxyalkylene group is preferably 1 to 10, more preferably 2 to 6, still more preferably 2 to 4.

The above polyoxyalkylene group is more preferably a polyoxyethylene group or a polyoxypropylene group.

A plurality of oxyalkylene groups of the above polyoxyalkylene group may be the same as or different from each other. The average number of repetitions of an oxyalkylene group of the above polyoxyalkylene group is preferably 2 to 1,000, more preferably 3 to 500. The average number of repetitions may also be 2 to 100, 2 to 50, 2 to 35, or 2 to 25.

When the above polyoxyalkylene group has a plurality of different oxyalkylene groups, the average number of repetitions of the oxyalkylene groups is the sum of the average number of repetitions of each oxyalkylene group. For example, the average number of repetitions in B-12 below is 2+9+2=13, and the average number of repetitions in B-15 below is 2+2+2=6.

Preferred specific examples of the polyamine compound (B) that can be used in the present invention are shown below. The number attached to parentheses is the average number of repetitions of the repeating unit in the parentheses.

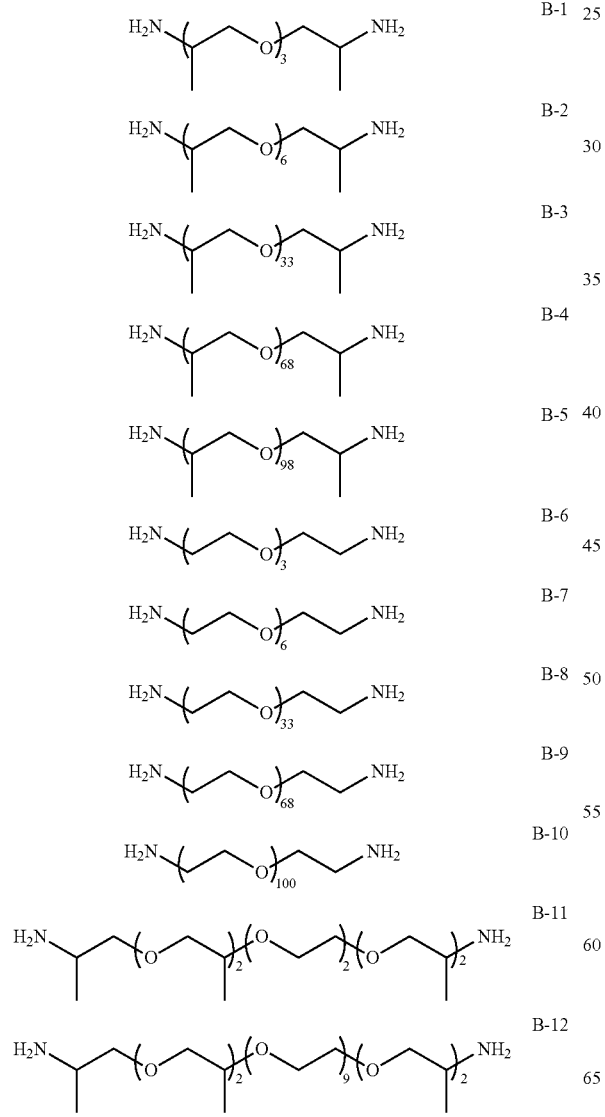
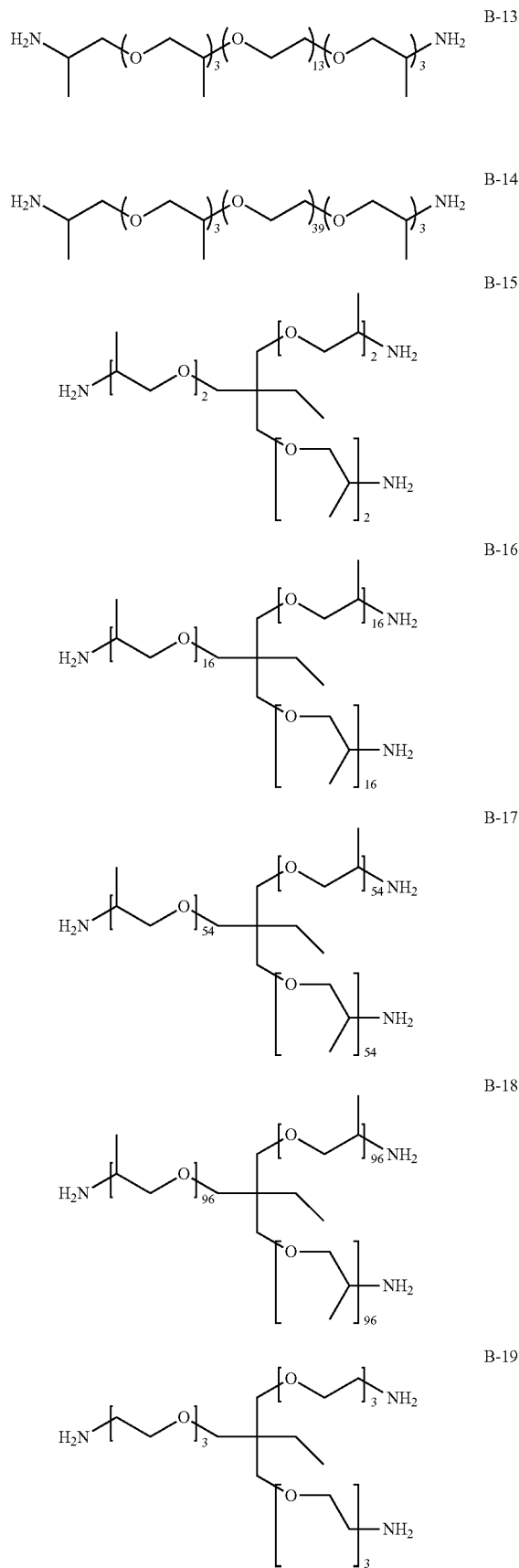

B-20
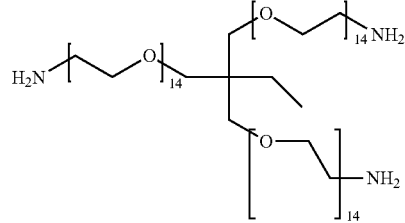
B-21
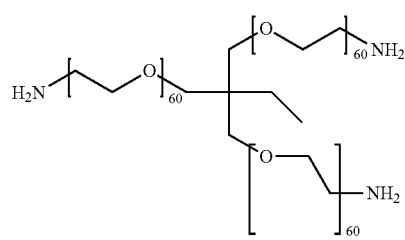
B-22
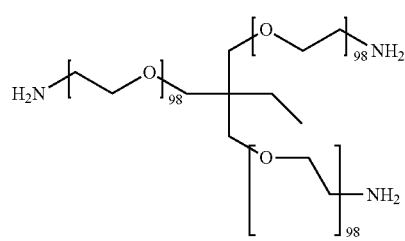
B-23
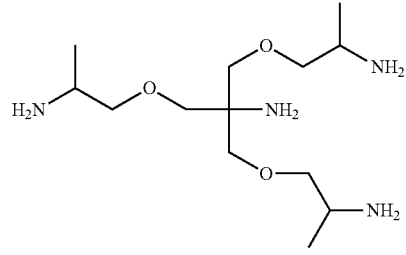
B-24
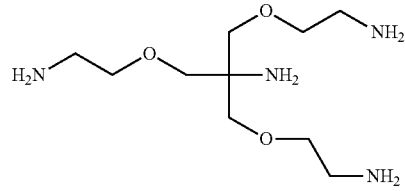
B-25
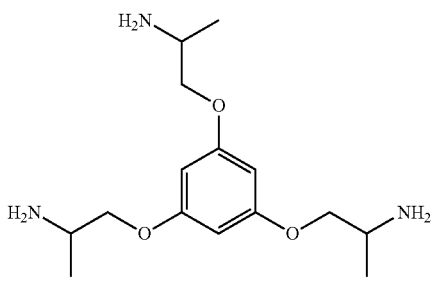
B-26
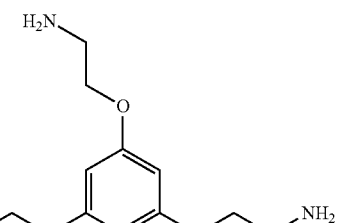
B-27
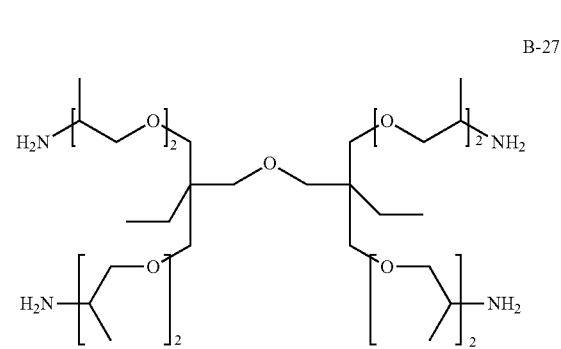
B-28
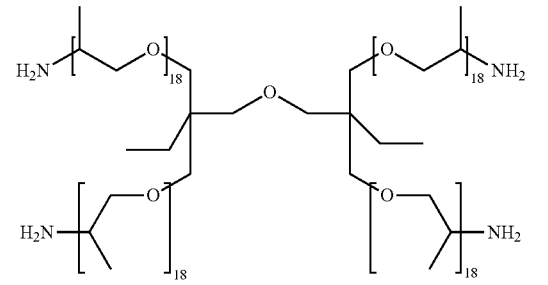
B-29
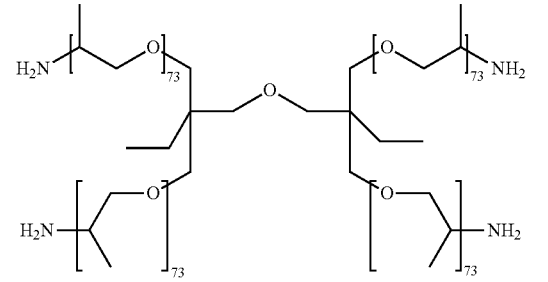
B-30
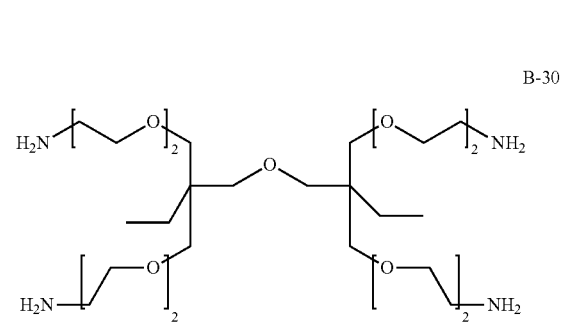

B-31
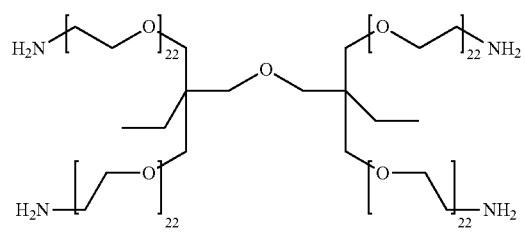
B-32
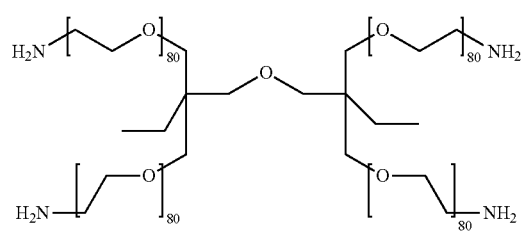
B-33
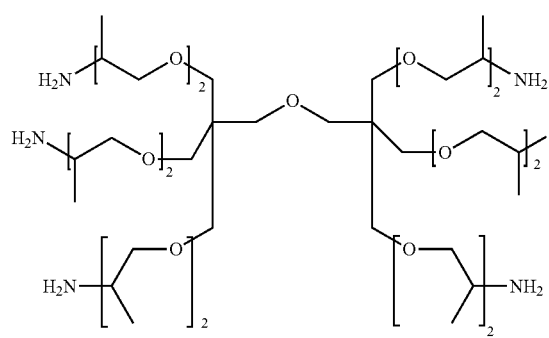
B-34
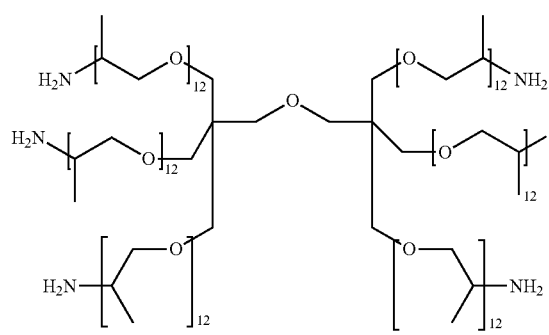
B-35
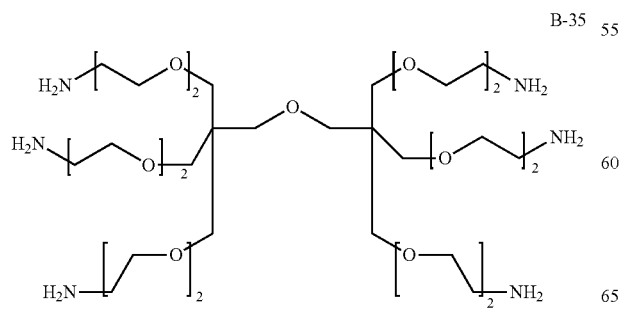
B-36
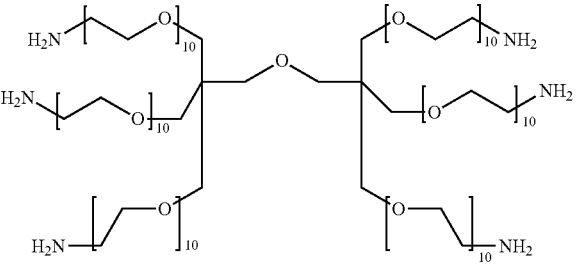
B-37
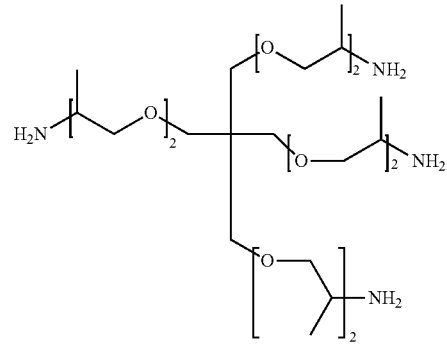
B-38
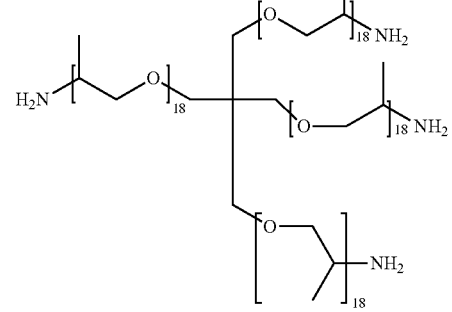
B-39
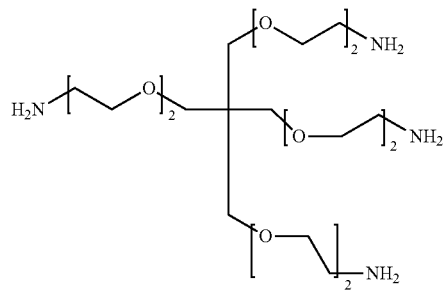
B-40
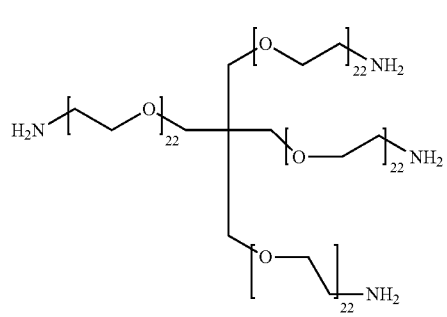

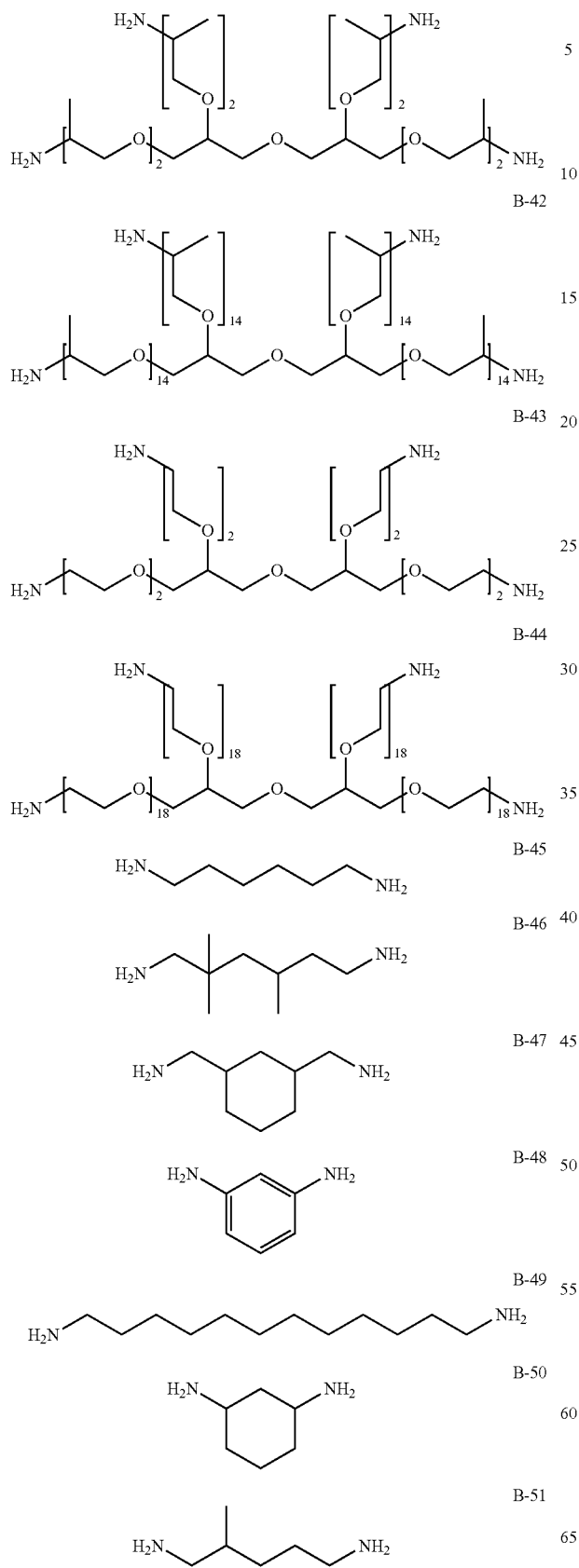

The polyamine compound (B) can be synthesized by a usual method. Alternatively, a commercially available product may be used.

The adhesive according to the present invention may contain a curing component other than the polyamine compound (B), and the proportion of the polyamine compound (B) in the whole curing component is preferably 80 mass % or more, more preferably 90 mass % or more. The whole curing component may be constituted by the polyamine compound (B). When the adhesive according to the present invention includes a curing component other than the polyamine compound (B), the curing component may be any curing agent or curing aid known as a curing component of an epoxy adhesive. For example, at least one of an acid anhydride compound, an imidazole compound, a phosphorus compound, a thiol compound, a dicyandiamide compound, or a phenolic compound may be used in combination with the polyamine compound (B).

Compound (C) Represented by General Formula (1)

The adhesive according to the present invention contains a compound (C) represented by general formula (1).

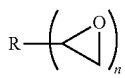

general formula (1)

In the formula, n represents an integer of 1 to 6. R represents an aliphatic hydrocarbon group, an alicyclic hydrocarbon group, an aromatic hydrocarbon group, a heterocyclic group (preferably an aromatic heterocyclic group), or a combination thereof, the groups and the combination each having a valence of n. R does not adopt a -phenylene-methylene-phenylene-structure or bind to an epoxy group in the formula to form a ring.

A group having a valence of n (an n-valent group) means a group in which n different atoms have free valences.

To further improve the sterilization resistance of the adhesive cured product, n is preferably an integer of 2 to 4. To further improve the low-temperature curability of the adhesive for an endoscope, n is more preferably 2 or 3. To further improve the flexibility of the adhesive cured product, n is still more preferably 2.

R is preferably an aliphatic hydrocarbon group, an alicyclic hydrocarbon group, an aromatic hydrocarbon group, or a combination thereof, the groups and the combination each having a valence of n.

The aliphatic hydrocarbon group and the alicyclic hydrocarbon group may each have a heteroatom in a carbon chain. However, a group that forms a structure in which the heteroatom and the epoxy group are directly bonded together (-heteroatom-epoxy group) in general formula (1) is excluded. Examples of the heteroatom include an oxygen atom, a nitrogen atom, and a sulfur atom, and an oxygen atom is preferred.

"Having a heteroatom in a carbon chain" means that the heteroatom is incorporated in the carbon chain as in —C—O—C— (ether bond). It is preferable not to include a configuration in which the heteroatom is not incorporated in the carbon chain like the oxygen atom of the carbonyl group in —C—C(=O)—O—C— (ester bond).

Examples of the n-valent aliphatic hydrocarbon group include n-valent saturated aliphatic hydrocarbon groups (an alkyl group, an alkylene group, an alkanetriyl group, an alkanetetrayl group, an alkanepentayl group, and an alkanehexayl group) and n-valent unsaturated aliphatic hydrocarbon groups (e.g., a group having a carbon-carbon double bond in the molecular chain of an alkyl group, an alkylene group, an alkanetriyl group, an alkanetetrayl group, an alkanepentayl group, or an alkanehexayl group but not having a ring structure). The aliphatic hydrocarbon group may be linear or branched. In particular, n-valent saturated aliphatic hydrocarbon groups are preferred.

Examples of the n-valent alicyclic hydrocarbon group include a cycloalkyl group, a cycloalkylene group, a cycloalkanetriyl group, a cycloalkanetetrayl group, a cycloalkanepentayl group, and a cycloalkanehexayl group.

Examples of the n-valent aromatic hydrocarbon group include an aryl group, an arylene group, an arenetriyl group, an arenetetrayl group, an arenepentayl group, and an arenehexayl group.

The n-valent aromatic heterocyclic group is the same as the above n-valent aromatic hydrocarbon group except for having a heteroatom in an aromatic ring. The number of heteroatoms in the aromatic ring is preferably 1 or 2, more preferably 1. Examples of the heteroatom include an oxygen atom, a nitrogen atom, and a sulfur atom, and an oxygen atom is preferred.

The above combined n-valent group is preferably a combination of at least two of an aliphatic hydrocarbon group, an alicyclic hydrocarbon group, an aromatic hydrocarbon group, or an aromatic heterocyclic group. A combination of two or three groups is more preferred, and a combination of two groups is still more preferred. Examples include a combination of an aliphatic hydrocarbon group and an alicyclic hydrocarbon group and a combination of an aliphatic hydrocarbon group and an aromatic hydrocarbon group.

The molecular weight of the compound (C) is not particularly limited, and is preferably 100 or more and less than 3,000, more preferably 120 or more and less than 1,500, still more preferably 200 or more and less than 1,000. When the compound (C) is a mixture of compounds with different n's or has a molecular weight distribution like an oligomer, the molecular weight means a mass average molecular weight.

The mass average molecular weight can be measured by the following method.

A GPC apparatus HLC-8220 (trade name, manufactured by Tosoh Corporation) is used. Tetrahydrofuran is used as an eluant, and G3000HXL+G2000HXL (trade names, manufactured by Tosoh Corporation) are used as columns. The detection is performed with an RI detector at 23° C. and a flow rate of 1 mL/min.

When the compound (C) is a single compound, the number of epoxy groups in one molecule of the compound (C) is n. When the compound (C) is a mixture of compounds with different n's, the number of epoxy groups in the compound (C) is the average number of epoxy groups calculated by the following formula. The average number of epoxy groups can be measured, for example, by NMR, GPC, or titration described below.

Average number of epoxy groups=(molecular weight)/(average epoxy equivalent)

The epoxy equivalent of the compound (C) is not particularly limited, and is preferably 100 or more and 1,000 or less, more preferably 180 or more and 600 or less. The epoxy equivalent is expressed as molecular weight/number of epoxy groups in one molecule. When the compound (C) is a mixture, the epoxy equivalent is calculated by the following formula, and can be measured, for example, by NMR, GPC, or a titration method described in JIS K 7236: 2009.

Average epoxy equivalent=(molecular weight)/(average number of epoxy groups)

The compound (C) may be liquid or solid. The viscosity at 20° C. of the compound (C) is preferably 5 mPa·s or more, more preferably 10 mPa·s or more, still more preferably 20 mPa·s or more. Although there is no particular upper limit, the viscosity is practically 1,000 mPa·s or less.

In the adhesive according to the present invention, the compound (C) is preferably an aliphatic polyhydric alcohol polyglycidyl ether. The term "aliphatic polyhydric alcohol polyglycidyl ether" refers to a compound represented by general formula (1) above, where n is an integer of 2 to 6, and R is an aliphatic hydrocarbon group, an alicyclic hydrocarbon group, or a combination thereof. By using an aliphatic polyhydric alcohol polyglycidyl ether as the compound (C), the viscosity of the adhesive can be reduced, and the transparency and sterilization resistance of the adhesive cured product can be further improved.

Specific examples of "aliphatic polyhydric alcohols (dihydric to hexahydric alcohols)" in the aliphatic polyhydric alcohol polyglycidyl ether include the following alcohols.

Dihydric Alcohol

Ethylene glycol, 1,2-propanediol, 1,3-propanediol, 1,3-butanediol, 1,4-butanediol, 1,5-pentanediol, neopentyl glycol, 1,6-hexanediol, diethylene glycol, triethylene glycol, tetraethylene glycol, polyethylene glycol, dipropylene glycol, polypropylene glycol, cyclohexane dimethanol Trihydric Alcohol Glycerol, trimethylolethane, trimethylolpropane Tetrahydric Alcohol Diglycerol, erythritol, pentaerythritol Pentahydric Alcohol Triglycerol Hexahydric Alcohol Dipentaerythritol The aliphatic polyhydric alcohol polyglycidyl ether used in the present invention can be obtained, for example, by a transesterification reaction between the above aliphatic polyhydric alcohol and an ester compound having a glycidyl group.

Specific examples of the aliphatic polyhydric alcohol polyglycidyl ether include 1,6-hexanediol diglycidyl ether, 1,4-butanediol diglycidyl ether, cyclohexanedimethanol diglycidyl ether, trimethylolpropane polyglycidyl ether, diethylene glycol diglycidyl ether, neopentyl glycol diglycidyl ether, propylene glycol diglycidyl ether, polypropylene glycol diglycidyl ether, polyethylene glycol diglycidyl ether, and sorbitol polyglycidyl ether.

Specific examples of the compound (C) are given below, but the present invention is not limited to these specific examples.

EPICLON 725 (trade name, manufactured by DIC Corporation)

RIKARESIN DME-100 (trade name, manufactured by New Japan Chemical Co., Ltd.)

BGE-C, SY-25L, SR-NPG, SR-16H, SR-16HL, SR-TMP, SR-PG, SR-TPG, SR-4PG, SR-2EG, SR-8EG, SR-2EGS, SR-BEGS, SR-GLG, SR-DGE, SR-SEP (trade names, manufactured by Sakamoto Yakuhin Kogyo Co., Ltd.)

PG-207GS, ZX-1658GS, ZX-1542 (trade names, manufactured by Nippon Steel & Sumikin Chemical Co., Ltd.)

DENACOL EX-121, DENACOL EX-141, DENACOL EX-146, DENACOL EX-611, DENACOL EX-612, DENACOL EX-614, DENACOL EX-614B, DENACOL EX-622, DENACOL EX-512, DENACOL EX-521, DENACOL EX-411, DENACOL EX-421, DENACOL EX-301, DENACOL EX-313, DENACOL EX-314, DENACOL EX-321, DENACOL EX-211, DENACOL EX-810, DENACOL EX-811, DENACOL EX-851, DENACOL EX-821, DENACOL EX-830, DENACOL EX-832, DENACOL EX-841, DENACOL EX-861, DENACOL EX-911, DENACOL EX-941, DENACOL EX-920, DENACOL EX-921, DENACOL EX-931, DENACOL EX-145, DENACOL EX-171, DENACOL EX-701 (trade names, manufactured by Nagase ChemteX Corporation)

EPOLIGHT 40E, EPOLIGHT 100E, EPOLIGHT 200E, EPOLIGHT 400E, EPOLIGHT 70P, EPOLIGHT 200P, EPOLIGHT 400P, EPOLIGHT 1500NP, EPOLIGHT 1600, EPOLIGHT 80MF, EPOLIGHT 100MF (trade names, manufactured by Kyoeisha Chemical Co., Ltd.)

EPIOL BE-200, EPIOL G-100, EPIOL E-100, EPIOL E-400, EPIOL E-1000, EPIOL P-200, EPIOL NPG-100, EPIOL TMP-100, EPIOL OH (trade names, manufactured by NOF Corporation)

ADK CIZER O-130P, ADK CIZER D-32 (trade names, manufactured by ADEKA Corporation)

In the adhesive according to the present invention, a single compound (C) may be used alone, or two or more compounds (C) may be used in combination.

Cured Product

A cured product according to the present invention is formed by curing the adhesive according to the present invention. That is, the cured product according to the present invention is used as a member constituting an adhesive joint of an endoscope. The cured product according to the present invention can be obtained by mixing together components included in the adhesive according to the present invention and then curing the mixture, for example, by settling or heating at 10° C. to 120° C. for 0.5 to 200 hours. The mixing of the components can be performed in the usual manner. The mixing is preferably performed while removing bubbles, and thus is usually performed under reduced pressure. If the curing temperature is high, the endoscope will be exposed to high temperature for many times during the production process, and thus the curing temperature is preferably as low as possible. From this viewpoint, the curing temperature is preferably 100° C. or lower, more preferably 80° C. or lower. For the curing reaction to sufficiently proceed, the curing temperature is preferably 10° C. or higher, more preferably 20° C. or higher.

Endoscope

An endoscope according to the present invention has an adhesive joint between a fixed member and a resin member, a metal member, or a glass member, the adhesive joint being formed of the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and mainly formed of a metal (e.g., stainless steel) member. An imaging device (not illustrated) for imaging a body cavity is built in the tip portion 3c. The flexible tube 3a, which occupies most of the length of the insertion section 3, is flexible over substantially the entire length thereof. In particular, a portion to be inserted into a body cavity or the like has a more flexible structure.

In FIG. 1, a plurality of channels (not illustrated) are formed that extend from the main-body operation section 5 to the distal end surface of the tip portion 3c through the insertion section 3 along the axis direction of the insertion section 3.

Figure 2:
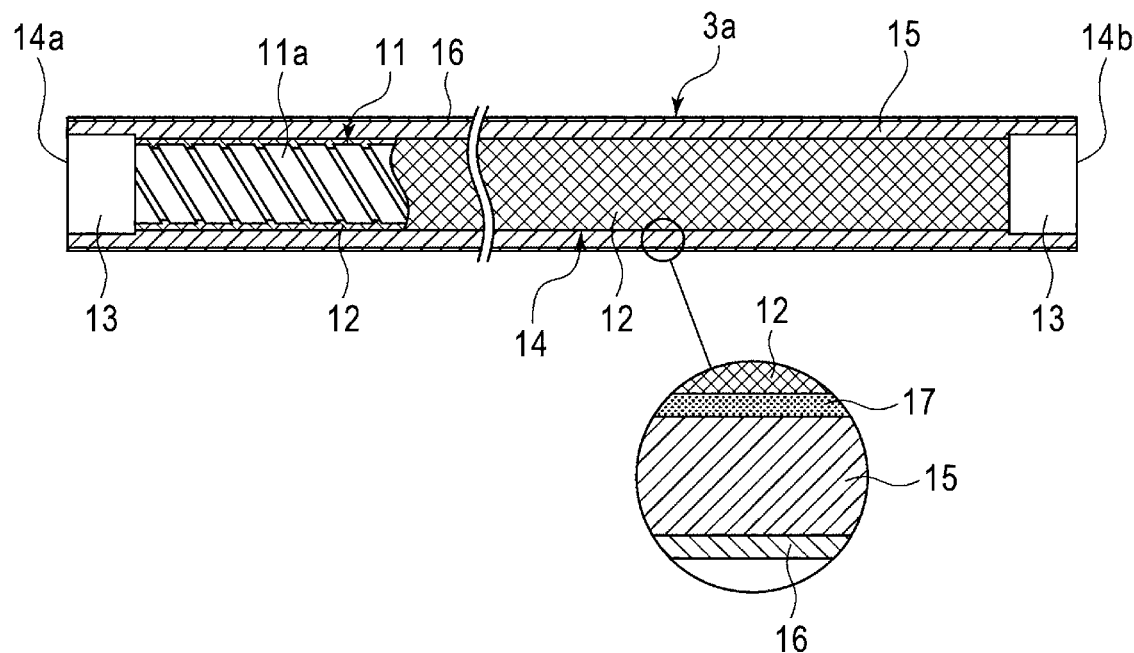
FIG. 2 is a partial sectional view illustrating a configuration of an insertion section of the endoscope illustrated in FIG. 1.

The flexible tube 3a in FIG. 1 is configured such that a resin layer 15 covers the outer peripheral surface of a flexible tube substrate 14, as illustrated in FIG. 2.

14a is the distal side (the tip portion 3c side), and 14b is the proximal side (the main-body operation section 5 side).

The flexible tube substrate 14 includes a spiral tube 11, which is disposed on the innermost side and formed by spirally winding a metal strip 11a, and a tubular net 12, which covers the spiral tube 11 and is formed by braiding metal wires. Caps 13 are fitted to opposite ends of the flexible tube substrate 14. The resin layer 15 is bonded to the flexible tube substrate 14 with an adhesive cured product layer 17 interposed therebetween. While the adhesive cured product layer (adhesive joint) 17 is illustrated as a layer having a uniform thickness for convenience of illustration, the adhesive cured product layer 17 need not necessarily be in such a form and may be indeterminately interposed between the resin layer 15 and the flexible tube substrate 14. The adhesive cured product layer 17 may rather have substantially no thickness such that the resin layer 15 and the flexible tube substrate 14 are substantially directly bonded together.

The outer surface of the resin layer 15 is coated with a coat layer 16 having chemical resistance and containing, for example, fluorine. To clearly illustrate the layer structure, the adhesive cured product layer 17, the resin layer 15, and the coat layer 16 are illustrated as being thick relative to the diameter of the flexible tube substrate 14.

Figure 3:
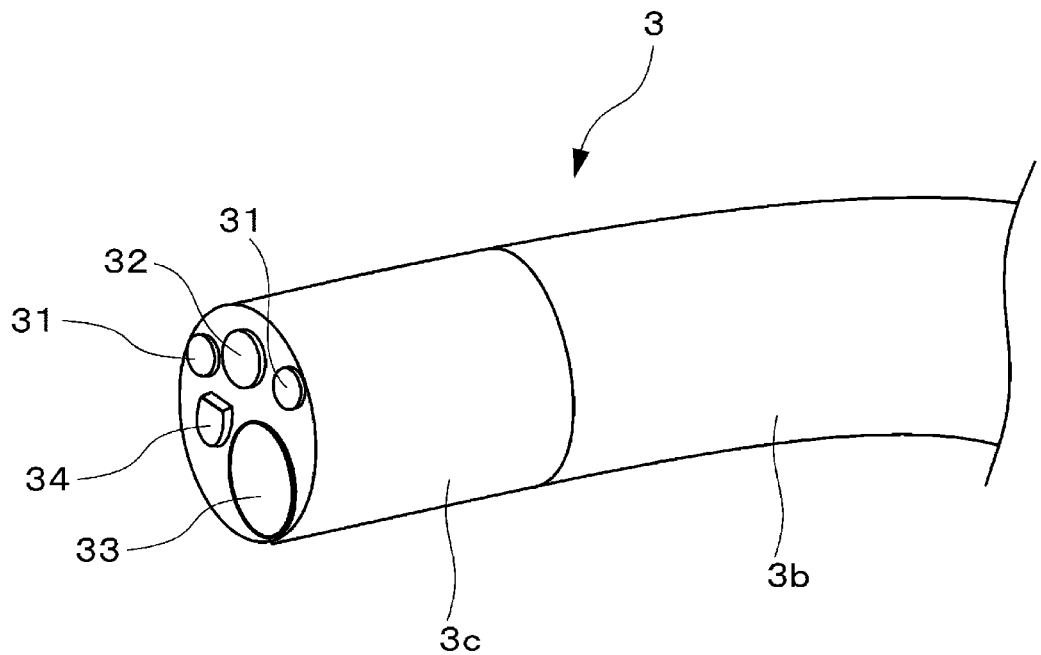
FIG. 3 is an external perspective view of a tip portion of the insertion section.

As illustrated in FIG. 3, an illumination window 31, an observation window 32, and a forceps port 33 are formed in the distal end surface of the tip portion 3c. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
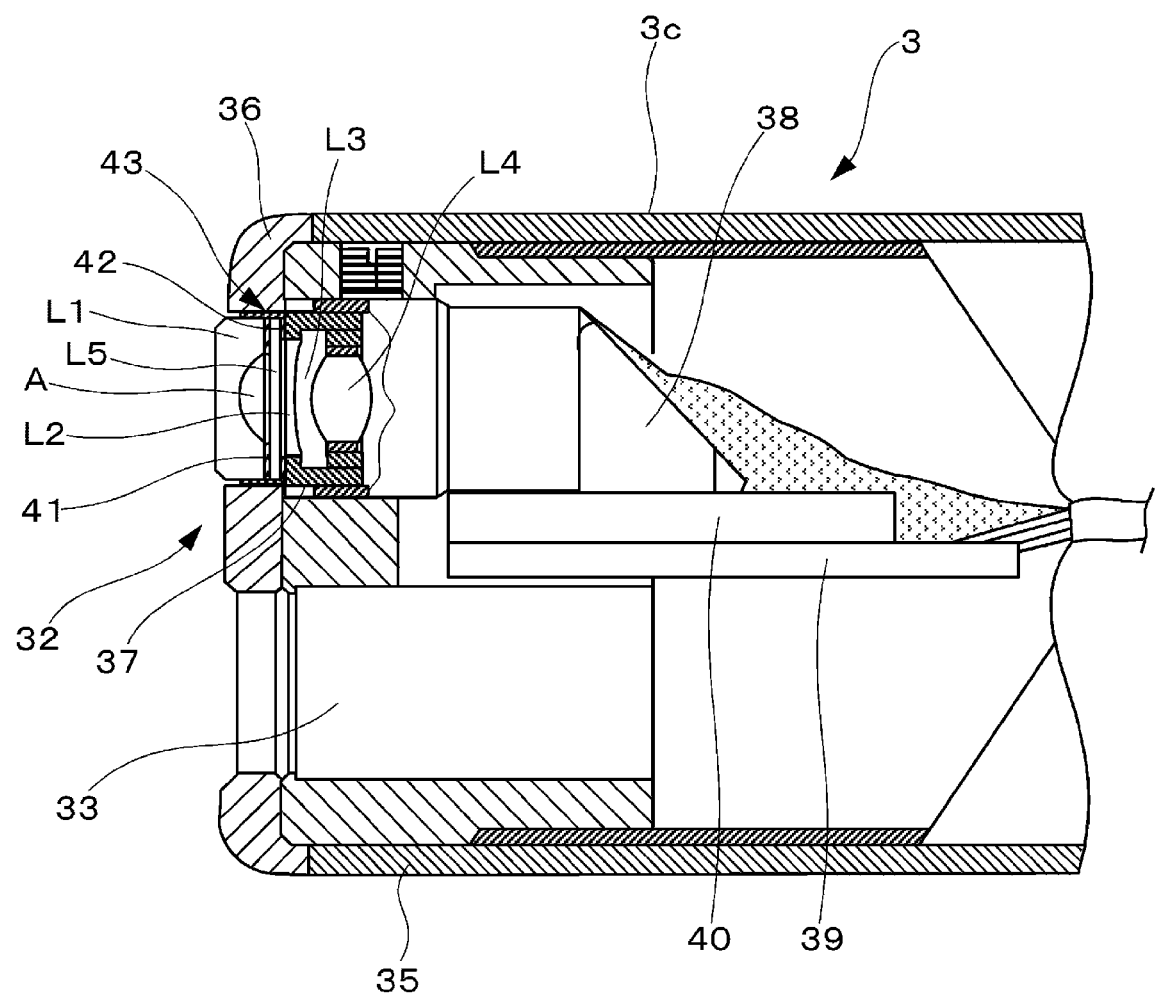
FIG. 4 is a partially cut-away partial sectional view of the tip portion, without hatching that shows sections of lenses and a prism.

As illustrated in FIG. 4, the tip portion 3c is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with adhesive cured products 41 and 42. In the objective optical system, A is an air layer. A prism 38 is bonded and fixed to an end face of the lens holder 37. The optical axis of the objective optical system can be bent at a right angle by the prism 38. The prism 38 is bonded to a solid-state imaging element 40. The solid-state imaging element 40 is fixed to a substrate 39.

Method for Producing Endoscope

A method for producing an endoscope according to the present invention is not particularly limited as long as the method includes fixing at least one of a resin member, a metal member, or a glass member by using the adhesive according to the present invention. For steps other than fixing of at least one of a resin member, a metal member, or a glass member, usual production steps can be employed to produce the endoscope according to the present invention. For example, the method for producing an endoscope according to the present invention preferably includes a step of mixing together the epoxy resin (A), the polyamine compound (B), and the compound (C) of the adhesive according to the present invention under reduced pressure, then injecting or applying the adhesive according to the present invention into or to a target portion, and heating the adhesive at 10° C. to 120° C. (preferably 20° C. to 100° C., more preferably 40° C. to 80° C.) for 0.5 to 24 hours.

Use of Adhesive

The adhesive according to the present invention is used to fix at least one of a resin member, a metal member, or a glass member constituting an insertion section of an endoscope to another member constituting the endoscope. That is, the fixing is performed by bonding at least one of a resin member, a metal member, or a glass member to a supporting member (e.g., a resin member, a glass member, or a metal member). Preferably, the adhesive according to the present invention is used to fix a resin member to a metal member, to fix a metal member to a resin member, or to fix a metal member to another metal member.

Specific examples of how the adhesive according to the present invention is used will be described below, but the present invention is not limited to these examples.

Examples of resin members include tubes inserted into an insertion section of an endoscope. The tubes include various tubes produced using various materials including fluorocarbon resins such as Teflon (registered trademark), resins such as polysulfone, polyester, polyolefin, and silicone, and rubber. The adhesive according to the present invention can be used, for example, to bond a metal member or a glass member constituting an insertion section of an endoscope to any of the above tubes (to fix the metal member or the glass member to any of the above tubes).

The adhesive according to the present invention can also be used to form the adhesive cured product layer 17 in FIG. 2. The adhesive according to the present invention can also be used to bond together the resin layer 15 and the coat layer 16 in FIG. 2.

The adhesive according to the present invention can be used for outer-surface finishing and fixing of an end of a flexible outer cover tube (the resin layer 15) (the end on the distal side (the angle portion 3b side) of the flexible tube 3a). Specifically, the flexible tube 3a and the angle portion 3b are bonded together using the adhesive according to the present invention. A string is tightly wound around a portion of the flexible tube 3a near the adhesive joint, a portion of the angle portion 3b near the adhesive joint, and the adhesive joint to reinforce the bonding. The configuration in which the outermost layer on the distal-side end of the flexible tube 3a and the flexible tube 3a side end of the angle portion 3b is formed of the adhesive according to the present invention reduces the likelihood of raveling of the string and facilitates the insertion of the insertion section 3 into a body cavity. The insertion section thus formed can maintain a bright appearance after sterilization.

The adhesive according to the present invention can be used for at least one of bonding of the tip portion 3c and the angle portion 3b or bonding of the insertion section 3 and the main-body operation section 5. Specifically, the tip portion 3c and the angle portion 3b are bonded together using the adhesive according to the present invention. A string is tightly wound around a portion of the tip portion 3c near the adhesive joint, a portion of the angle portion 3b near the adhesive joint, and the adhesive joint to reinforce the bonding. In the same manner as described above, the adhesive is applied so as to coat the string and cured. The bonding of the insertion section 3 and the main-body operation section 5 is performed in the same manner.

Preferably, the adhesive according to the present invention is used to fix various tubes inserted into the insertion section of the endoscope to at least one of the tip portion 3c or the main-body operation section 5.

The adhesive according to the present invention is preferably used for the tip portion 3c. Among the uses for the tip portion 3c, the adhesive according to the present invention is preferably used to seal the illumination window 31 and the observation window 32 (to fix the glass members). This is because a thick coating of the adhesive according to the present invention can smoothen the outer corners of the lenses and block the entrance of light from the lateral sides of the lenses.

The adhesive according to the present invention can be used to fix at least one of a metal member or a glass member, for example, to assemble the imaging device built in the tip portion 3c, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, for bonding of optical parts including the lenses L1 to L5 and the prism 38 made of materials such as glass and bonding of at least one of the lenses L1 to L5 and the prism 38 to the substrate 39 made of resin or metal. This bonding can fix the glass members and can fix the metal member.

The adhesive according to the present invention can be used for bond-fixing and sealing of the solid-state imaging element 40 and the substrate 39. This bonding can fix the metal members constituting the solid-state imaging element, the substrate, and the like.

EXAMPLES

The present invention will now be described in more detail with reference to examples. These examples should not be construed as limiting the present invention. "Room temperature" means 25° C.

Preparation of Adhesive for Endoscope (Example 1) and Production of Sheet-Like Adhesive Cured Product (Example 1)

Using a "THINKY MIXER ARV-310 (manufactured by THINKY CORPORATION)", 100 parts by mass of an epoxy resin (A-1) (bisphenol A diglycidyl ether ("jER825" (trade name) manufactured by Mitsubishi Chemical Corporation, epoxy equivalent: 170)), 25 parts by mass of a polyamine compound (B-1) (1,6-hexanediamine (manufactured by Tokyo Chemical Industry Co., Ltd., active hydrogen equivalent: 29)), and 25 parts by mass of a compound (C-1) (polyethylene glycol diglycidyl ether ("SR-BEGS" manufactured by Sakamoto Yakuhin Kogyo Co., Ltd., the number of functional groups: 2 (n in general formula (1)=2))) were defoamed for 5 minutes with stirring at 2,000 rpm under a reduced pressure of 1.0 Pa at room temperature to obtain an adhesive for an endoscope of Example 1.

The adhesive for an endoscope of Example 1 was poured into a Teflon (registered trademark) mold of 100 mm long× 20 mm wide×0.4 mm thick and allowed to sit at 30° C. for 170 hours, thereby obtaining a sheet-like adhesive cured product of Example 1. Hereinafter, the sheet-like adhesive cured product is also referred to as the "sheet-like cured product". Preparation of adhesives for endoscope (Examples 2 to 40 and Comparative Examples 1 to 3) and production of sheet-like adhesive cured products (Examples 2 to 40 and Comparative Examples 1 to 3)

Adhesives for an endoscope of Examples 2 to 40 and Comparative Examples 1 to 3 were prepared in the same manner as the adhesive for an endoscope of Example 1 except that the composition was changed as shown in Table 1 given below, and sheet-like cured products of Examples 2 to 40 and Comparative Examples 1 to 3 were produced.

In Comparative Examples 2 and 3, compounds (X-1) and (X-2) not falling within the scope of general formula (1) above were used in place of the compound (C).

Low-Temperature Curability Test

Using an FT-IR ("Nicolet MAGNA760 (trade name) FT-IR spectrometer" manufactured by GMI), the absorbance peak area of an oxirane ring at 790 cm$^{-1}$ was measured. The value measured immediately after being poured into a Teflon mold was assumed to be 100 area %, and the value (area %) of absorbance peak area measured after being allowed to sit at 30° C. for 170 hours was subtracted from 100 area % to thereby determine the reaction rate of epoxy groups of the compound (C). The calculated value was evaluated according to the following criteria. A, B, and C are acceptable in this test. The results are shown in Table 1 given below.

Evaluation Criteria

A: The epoxy reaction rate is 96 area % or more.

B: The epoxy reaction rate is 93 area % or more and less than 96 area %.

C: The epoxy reaction rate is 90 area % or more and less than 93 area %.

D: The epoxy reaction rate is less than 90 area %.

Flexibility Test

The sheet-like cured products obtained above were each wound around columns having different curvatures. The occurrence of cracking or breakage was visually observed and evaluated according to the following criteria. A, B, and C are acceptable in this test. The results are shown in Table 1 given below.

Evaluation Criteria

A: Neither cracking nor breakage occurred when a column having a diameter of 2 cm was used.

B: Cracking or breakage occurred when a column having a diameter of 2 cm was used, and neither cracking nor breakage occurred when a column having a diameter of 5 cm was used.

C: Cracking or breakage occurred when a column having a diameter of 5 cm was used, and neither cracking nor breakage occurred when a column having a diameter of 10 cm was used.

D: Cracking or breakage occurred when a column having a diameter of 10 cm was used.

Transparency Test (Bleed Resistance Test)

The sheet-like cured products obtained above were each left to stand in a constant temperature and humidity environment at a temperature of 85° C. and a relative humidity of 90% for 7 days. The haze value of the sheet was measured in accordance with JIS K 7105 using a turbidimeter ("NDH5000" (trade name) manufactured by Nippon Denshoku Industries Co., Ltd.), and the measured value was evaluated according to the following criteria. A, B, and C are acceptable in this test. Smaller haze values indicate higher transparency of the sheet and higher bleed resistance (tendency of the compound (C) not to bleed out).

Evaluation Criteria

A: The haze value is 0.5% or less.

B: The haze value is more than 0.5% and 1.0% or less.

C: The haze value is more than 1.0% and 3.0% or less.

D: The haze value is more than 3.0%.

Hydrogen Peroxide Plasma Sterilization Resistance Test

Using a STERRAD (registered trademark) NX (trade name, manufactured by Johnson & Johnson) advanced course, a hydrogen peroxide plasma sterilization treatment was performed on the above sheet-like cured products at room temperature. Using an Autograph AGS-X (trade name, manufactured by Shimadzu Corporation), a sheet-like cured product before the sterilization treatment and a sheet-like cured product subjected to the sterilization treatment 100 times were subjected to an elongation tensile test in which each sheet-like cured product was stretched in the longitudinal (lengthwise) direction at a tensile speed of 20 mm/min with a chuck distance set to 20 mm. The sterilization resistance was evaluated on the basis of a breaking strength retention after the sterilization treatment (100×[breaking strength (MPa) after 100 sterilization treatments]/[breaking strength (MPa) before sterilization treatment]). In the following evaluation criteria, A, B, and C are acceptable in this test. The results are shown in Table 1 given below.

Evaluation Criteria

A: The breaking strength is 95% or more of that before a sterilization treatment.

B: The breaking strength is 90% or more and less than 95% of that before a sterilization treatment.

C: The breaking strength is 85% or more and less than 90% of that before a sterilization treatment.

D: The sample is degraded and broken during a hydrogen peroxide plasma sterilization treatment, and a tensile test cannot be performed.

[Smaller Decreases Indicate that the Cured Product has Undergone Less Oxidation Degradation.]

TABLE 1

|  |  |  | Ex. 1 | Ex. 2 | Ex. 3 | Ex. 4 | Ex. 5 | Ex. 6 |
|---|---|---|---|---|---|---|---|---|
| Adhesive composition | Epoxy resin (A) | Type | (A-1) | (A-2) | (A-3) | (A-4) | (A-5) | (A-1) |
|  |  | Content [parts by mass] | 100 | 100 | 100 | 100 | 100 | 100 |
|  | Polyamine compound (B) | Type | (B-I-1) | (B-I-1) | (B-I-1) | (B-I-1) | (B-I-1) | (B-I-2) |
|  |  | Content [parts by mass] | 25 | 25 | 25 | 25 | 25 | 25 |
|  | Compound (C) | Type | (C-1) | (C-1) | (C-1) | (C-1) | (C-1) | (C-1) |
|  |  | Number of functional groups | 2 | 2 | 2 | 2 | 2 | 2 |
|  |  | Content [parts by mass] | 25 | 25 | 25 | 25 | 25 | 25 |
|  | Component (D) | Type | — | — | — | — | — | — |
|  |  | Content [parts by mass] |  |  |  |  |  |  |
| Evaluation |  | Low-temperature curability | A | A | A | A | A | A |
|  |  | Flexibility | A | A | A | A | A | A |
|  |  | Bleed resistance | A | A | A | A | A | A |
|  |  | Sterilization resistance | B | B | B | B | B | B |

|  |  |  | Ex. 7 | Ex. 8 | Ex. 9 | Ex. 10 |
|---|---|---|---|---|---|---|
| Adhesive composition | Epoxy resin (A) | Type | (A-1) | (A-1) | (A-1) | (A-1) |
|  |  | Content [parts by mass] | 100 | 100 | 100 | 100 |
|  | Polyamine compound (B) | Type | (B-I-3) | (B-I-4) | (B-I-5) | (B-I-6) |
|  |  | Content [parts by mass] | 25 | 25 | 25 | 25 |
|  | Compound (C) | Type | (C-1) | (C-1) | (C-1) | (C-1) |
|  |  | Number of functional groups | 2 | 2 | 2 | 2 |
|  |  | Content [parts by mass] | 25 | 25 | 25 | 25 |
|  | Component (D) | Type | — | — | — | — |
|  |  | Content [parts by mass] |  |  |  |  |
| Evaluation |  | Low-temperature curability | A | B | A | A |
|  |  | Flexibility | A | B | B | A |
|  |  | Bleed resistance | A | A | A | A |
|  |  | Sterilization resistance | B | B | B | A |

|  |  |  | Ex. 11 | Ex. 12 | Ex. 13 | Ex. 14 | Ex. 15 | Ex. 16 |
|---|---|---|---|---|---|---|---|---|
| Adhesive composition | Epoxy resin (A) | Type | (A-1) | (A-1) | (A-1) | (A-1) | (A-1) | (A-1) |
|  |  | Content [parts by mass] | 100 | 100 | 100 | 100 | 100 | 100 |
|  | Polyamine compound (B) | Type | (B-I-7) | (B-I-8) | (B-I-9) | (B-I-10) | (B-I-11) | (B-I-12) |
|  |  | Content [parts by mass] | 25 | 25 | 25 | 25 | 25 | 25 |
|  | Compound (C) | Type | (C-1) | (C-1) | (C-1) | (C-1) | (C-1) | (C-1) |
|  |  | Number of functional groups | 2 | 2 | 2 | 2 | 2 | 2 |
|  |  | Content [parts by mass] | 25 | 25 | 25 | 25 | 25 | 25 |
|  | Component (D) | Type | — | — | — | — | — | — |
|  |  | Content [parts by mass] |  |  |  |  |  |  |
| Evaluation |  | Low-temperature curability | A | A | A | C | C | B |
|  |  | Flexibility | A | A | A | C | B | B |
|  |  | Bleed resistance | A | A | A | A | A | A |
|  |  | Sterilization resistance | A | A | B | C | C | B |

|  |  |  | Ex. 17 | Ex. 18 | Ex. 19 | Ex. 20 |
|---|---|---|---|---|---|---|
| Adhesive composition | Epoxy resin (A) | Type | (A-1) | (A-1) | (A-1) | (A-1) |
|  |  | Content [parts by mass] | 100 | 100 | 100 | 100 |
|  | Polyamine compound (B) | Type | (B-I-13) | (B-I-1) | (B-I-1) | (B-I-1) |
|  |  | Content [parts by mass] | 25 | 25 | 25 | 25 |
|  | Compound (C) | Type | (C-1) | (C-2) | (C-3) | (C-4) |
|  |  | Number of functional groups | 2 | 2 | 2 | 2 |
|  |  | Content [parts by mass] | 25 | 25 | 25 | 25 |
|  | Component (D) | Type | — | — | — | — |
|  |  | Content [parts by mass] |  |  |  |  |
| Evaluation |  | Low-temperature curability | A | A | A | A |
|  |  | Flexibility | B | A | A | A |
|  |  | Bleed resistance | A | A | A | A |
|  |  | Sterilization resistance | C | B | B | A |

TABLE 2

|  |  |  | Ex. 21 | Ex. 22 | Ex. 23 | Ex. 24 | Ex. 25 | Ex. 26 |
|---|---|---|---|---|---|---|---|---|
| Adhesive composition | Epoxy resin (A) | Type | (A-1) | (A-1) | (A-1) | (A-1) | (A-1) | (A-1) |
|  |  | Content [parts by mass] | 100 | 100 | 100 | 100 | 100 | 100 |
|  | Polyamine compound (B) | Type | (B-I-1) | (B-I-1) | (B-I-1) | (B-I-1) | (B-I-1) | (B-I-1) |
|  |  | Content [parts by mass] | 25 | 25 | 25 | 25 | 25 | 25 |

TABLE 2-continued

|  |  |  |  | (C-5) | (C-6) | (C-7) | (C-8) | (C-9) | (C-10) |
|---|---|---|---|---|---|---|---|---|---|
|  |  | Compound (C) | Type | | | | | | |
|  |  |  | Number of functional groups | 2 | 3 | 3 | 4 | 4 | 6 |
|  |  |  | Content [parts by mass] | 25 | 25 | 25 | 25 | 25 | 25 |
|  |  | Component (D) | Type | — | — | — | — | — | — |
|  |  |  | Content [parts by mass] | | | | | | |
| Evaluation |  | Low-temperature curability | | A | A | A | B | B | C |
|  |  | Flexibility | | A | B | B | B | B | C |
|  |  | Bleed resistance | | A | A | A | A | A | A |
|  |  | Sterilization resistance | | A | B | B | B | B | C |

|  |  |  |  | Ex. 27 | Ex. 28 | Ex. 29 | Ex. 30 |
|---|---|---|---|---|---|---|---|
| Adhesive composition | Epoxy resin (A) | Type | | (A-1) | (A-1) | (A-1) | (A-1) |
|  |  | Content [parts by mass] | | 100 | 100 | 100 | 100 |
|  | Polyamine compound (B) | Type | | (B-I-1) | (B-I-1) | (B-I-1) | (B-I-1) |
|  |  | Content [parts by mass] | | 25 | 25 | 25 | 25 |
|  | Compound (C) | Type | | (C-11) | (C-12) | (C-13) | (C-16) |
|  |  | Number of functional groups | | 1 | 1 | 1 | 1 |
|  |  | Content [parts by mass] | | 25 | 25 | 25 | 25 |
|  | Component (D) | Type | | — | — | — | — |
|  |  | Content [parts by mass] | | | | | |
| Evaluation | Low-temperature curability | | | A | A | A | A |
|  | Flexibility | | | C | B | A | A |
|  | Bleed resistance | | | B | B | B | C |
|  | Sterilization resistance | | | C | C | C | C |

|  |  |  | Ex. 31 | Ex. 32 | Ex. 33 | Ex. 34 | Ex. 35 | Ex. 36 |
|---|---|---|---|---|---|---|---|---|
| Adhesive composition | Epoxy resin (A) | Type | (A-1) | (A-1) | (A-1) | (A-1) | (A-1) | (A-1) |
|  |  | Content [parts by mass] | 100 | 100 | 100 | 100 | 100 | 100 |
|  | Polyamine compound (B) | Type | (B-I-1) | (B-I-1) | (B-I-1) | (B-I-1) | (B-I-1) | (B-I-1) |
|  |  | Content [parts by mass] | 25 | 25 | 25 | 25 | 25 | 25 |
|  | Compound (C) | Type | (C-14) | (C-15) | (C-1) | (C-1) | (C-1) | (C-1) |
|  |  | Number of functional groups | 1 | 1 | 2 | 2 | 2 | 2 |
|  |  | Content [parts by mass] | 25 | 25 | 5 | 10 | 15 | 40 |
|  | Component (D) | Type | — | — | — | — | — | — |
|  |  | Content [parts by mass] | | | | | | |
| Evaluation | Low-temperature curability | | A | A | A | A | A | A |
|  | Flexibility | | C | B | C | B | A | A |
|  | Bleed resistance | | B | B | A | A | A | A |
|  | Sterilization resistance | | C | C | C | B | B | B |

|  |  |  |  | Ex. 37 | Ex. 38 | Ex. 39 | Ex. 40 |
|---|---|---|---|---|---|---|---|
| Adhesive composition | Epoxy resin (A) | Type | | (A-1) | (A-1) | (A-1) | (A-1) |
|  |  | Content [parts by mass] | | 100 | 100 | 100 | 100 |
|  | Polyamine compound (B) | Type | | (B-I-1) | (B-I-1) | (B-I-1) | (B-I-1) |
|  |  | Content [parts by mass] | | 25 | 25 | 25 | 25 |
|  | Compound (C) | Type | | (C-1) | (C-4) | (C-1) | (C-1) |
|  |  | Number of functional groups | | 2 | 2 | 2 | 2 |
|  |  | Content [parts by mass] | | 50 | 25 | 25 | 25 |
|  | Component (D) | Type | | — | — | (D-1) | (D-2) |
|  |  | Content [parts by mass] | | | | 20 | 20 |
| Evaluation | Low-temperature curability | | | B | A | A | A |
|  | Flexibility | | | A | A | A | A |
|  | Bleed resistance | | | B | A | A | A |
|  | Sterilization resistance | | | C | A | A | A |

TABLE 3

|  |  |  | Comparative Example 1 | Comparative Example 2 | Comparative Example 3 |
|---|---|---|---|---|---|
| Adhesive composition | Epoxy resin (A) | Type | (A-1) | (A-1) | (A-1) |
|  |  | Content [parts by mass] | 100 | 100 | 100 |
|  | Polyamine compound (B) | Type | (B-I-1) | (B-I-1) | (B-I-1) |
|  |  | Content [parts by mass] | 25 | 25 | 25 |
|  | Compound (C) | Type | — | (X-1) | (X-2) |
|  |  | Number of functional groups | | 0 | 0 |
|  |  | Content [parts by mass] | | 25 | 25 |
|  | Component (D) | Type | — | — | — |
|  |  | Content [parts by mass] | | | |

TABLE 3-continued

|  |  | Comparative Example 1 | Comparative Example 2 | Comparative Example 3 |
|---|---|---|---|---|
| Evaluation | Low-temperature curability | D | A | A |
|  | Flexibility | D | A | A |
|  | Bleed resistance | A | D | D |
|  | Sterilization resistance | D | D | D |

Notes of Tables

"Ex." denotes Example. For example, Ex. 1 means Example 1.

Epoxy Compound (A)
- (A-1) Bisphenol A diglycidyl ether ("jER825" (trade name) manufactured by Mitsubishi Chemical Corporation, epoxy equivalent: 170)
- (A-2) Bisphenol A diglycidyl ether ("jER828" (trade name) manufactured by Mitsubishi Chemical Corporation, epoxy equivalent: 190)
- (A-3) Bisphenol A diglycidyl ether ("jER834" (trade name) manufactured by Mitsubishi Chemical Corporation, epoxy equivalent: 230)
- (A-4) Bisphenol F diglycidyl ether ("EPICLON 830" (trade name) manufactured by DIC Corporation, epoxy equivalent: 170)
- (A-5) Epoxy novolac resin (manufactured by Sigma-Aldrich, product number 406775, epoxy equivalent: 170)

Polyamine Compound (B)

B-I-1:
  1,6-Hexanediamine (manufactured by Tokyo Chemical Industry Co., Ltd., active hydrogen equivalent: 29)
  (Specific exemplary polyamine compound B-45 given above)

B-I-2:
  1,12-Dodecanediamine (manufactured by Tokyo Chemical Industry Co., Ltd., active hydrogen equivalent: 50)
  (Specific exemplary polyamine compound B-49 given above)

B-I-3:
  Trimethylhexamethylenediamine (manufactured by Tokyo Chemical Industry Co., Ltd., active hydrogen equivalent: 40)
  (Specific exemplary polyamine compound B-46 given above)

B-I-4:
  1,3-Cyclohexanediamine (manufactured by Tokyo Chemical Industry Co., Ltd., active hydrogen equivalent: 29)
  (Specific exemplary polyamine compound B-50 given above)

B-I-5:
  1,3-Bis(aminomethyl)cyclohexane (manufactured by Mitsubishi Gas Chemical Company, Inc., active hydrogen equivalent: 36)
  (Specific exemplary polyamine compound B-47 given above)

B-I-6:
  Polyoxyalkylenediamine D400 (trade name, manufactured by Mitsui Fine Chemicals, Inc., active hydrogen equivalent: 100)

B-I-7:
  Polyoxyalkylenediamine D2000 (trade name, manufactured by Mitsui Fine Chemicals, Inc., active hydrogen equivalent: 500)

B-I-8:
  Polyoxyalkylenetriamine T403 (trade name, manufactured by Mitsui Fine Chemicals, Inc., active hydrogen equivalent: 73)

B-I-9:
  2-Methylpentamethylenediamine (manufactured by Tokyo Chemical Industry Co., Ltd., active hydrogen equivalent: 29)
  (Specific exemplary polyamine compound B-51 given above)

B-I-10:
  m-Phenylenediamine (manufactured by Tokyo Chemical Industry Co., Ltd., active hydrogen equivalent: 27)
  (Specific exemplary polyamine compound B-48 given above)

B-I-11:
  4,4'-Methylenedianiline (manufactured by Tokyo Chemical Industry Co., Ltd., active hydrogen equivalent: 53)
  (Specific exemplary polyamine compound B-54 given above)

B-I-12:
  m-Xylylenediamine (manufactured by Tokyo Chemical Industry Co., Ltd.) (Specific exemplary polyamine compound B-53 given above)

B-I-13:
  N,N'-Dimethyl-1,6-diaminohexane (manufactured by Tokyo Chemical Industry Co., Ltd.)
  (Specific exemplary polyamine compound B-55 given above)

Compound (C)
- (C-1) Polyethylene glycol diglycidyl ether ("SR-BEGS" (trade name) manufactured by Sakamoto Yakuhin Kogyo Co., Ltd., the number of functional groups (the number of epoxy groups): 2, mass average molecular weight: 530)
- (C-2) Diethylene glycol diglycidyl ether ("SR-2EGS" (trade name) manufactured by Sakamoto Yakuhin Kogyo Co., Ltd., the number of functional groups: 2)
- (C-3) 1,6-Hexanediol diglycidyl ether ("SR-16H" (trade name) manufactured by Sakamoto Yakuhin Kogyo Co., Ltd., the number of functional groups: 2)
- (C-4) Tripropylene glycol diglycidyl ether ("SR-TPG" (trade name) manufactured by Sakamoto Yakuhin Kogyo Co., Ltd., the number of functional groups: 2)
- (C-5) Polypropylene glycol diglycidyl ether ("SR-4PG" (trade name) manufactured by Sakamoto Yakuhin Kogyo Co., Ltd., the number of functional groups: 2, mass average molecular weight: 610)
- (C-6) Glycerol triglycidyl ether ("SR-GLG" (trade name) manufactured by Sakamoto Yakuhin Kogyo Co., Ltd., the number of functional groups: 3)
- (C-7) Epoxidized soybean oil ("ADK CIZER 0-130P" (trade name) manufactured by ADEKA Corporation, the average number of functional groups: 3, mass average molecular weight: 570)
- (C-8) Diglyceroltetraglycidyl ether ("SR-DGE" (trade name) manufactured by Sakamoto Yakuhin Kogyo Co., Ltd., the number of functional groups: 4)

(C-9) Pentaerythritol tetraglycidyl ether ("DENACOL EX-411" (trade name) manufactured by Nagase ChemteX Corporation, the number of functional groups: 4)
(C-10) Sorbitol polyglycidyl ether ("SR-SEP" (trade name) manufactured by Sakamoto Yakuhin Kogyo Co., Ltd., the average number of functional groups: 6)
(C-11) Butyl glycidyl ether ("BGE-C" (trade name) manufactured by Sakamoto Yakuhin Kogyo Co., Ltd., the number of functional groups: 1)
(C-12) 2-Ethylhexyl glycidyl ether ("DENACOL EX-121" (trade name) manufactured by Nagase ChemteX Corporation, the number of functional groups: 1)
(C-13) Higher alcohol glycidyl ether ("SY-25L" (trade name) manufactured by Sakamoto Yakuhin Kogyo Co., Ltd., the number of functional groups: 1, molecular weight: 260)
(C-14) Epoxidized fatty acid octyl ester ("ADK CIZER D-32" (trade name) manufactured by ADEKA Corporation, the number of functional groups: 1, mass average molecular weight: 409)
(C-15) Phenyl glycidyl ether ("DENACOL EX-141" (trade name) manufactured by Nagase ChemteX Corporation, the number of functional groups: 1)
(C-16) 4-t-Butylphenyl glycidyl ether ("DENACOL EX-146" (trade name) manufactured by Nagase ChemteX Corporation, the number of functional groups: 1)
(X-1) Dioctyl phthalate ("SANSO CIZER DOP" manufactured by New Japan Chemical Co., Ltd., no functional groups)
(X-2) Liquid paraffin ("Mediaplast PX-2" (trade name) manufactured by Techno Preknead HIDA Co., Ltd., no functional groups) Component (D)
(D-1) Trimethylolpropane (reagent manufactured by Tokyo Chemical Industry Co., Ltd.)
(D-2) Polyvinyl alcohol ("POVAL PVA102" (trade name) manufactured by Kuraray Co., Ltd.)

As is clear from Tables 1 to 3, the adhesive of Comparative Example 1 does not contain the compound (C) of the present invention and thus has low low-temperature curability, and the adhesive cured product of Comparative Example 1 has low flexibility and low sterilization resistance. The adhesive cured products of Comparative Examples 2 and 3 have low bleed resistance and low sterilization resistance because the compounds (X-1) and (X-2) contained in the adhesives of Comparative Examples 2 and 3 are not incorporated, as constituents, into the adhesive cured products.

In contrast, the adhesives of Examples 1 to 40 have high low-temperature curability, and the adhesive cured products of Examples 1 to 40 have high flexibility, high bleed resistance, and high sterilization resistance.

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 2 electronic endoscope (endoscope)
3 insertion section
3a flexible tube
3b angle portion
3c tip portion
5 main-body operation section
6 universal cord
11 spiral tube
11a metal strip
12 tubular net
13 cap
14 flexible tube substrate
14a distal side
14b proximal side
15 resin layer
16 coat layer
17 adhesive cured product layer
31 illumination window
32 observation window
33 forceps port
34 nozzle
35 tip-portion main body
36 end cap
37 lens holder
38 prism
39 substrate
40 solid-state imaging element
41 adhesive cured product
42 adhesive cured product
43 observation unit
A air layer
L1 to L5 lens

What is claimed is:

1. An adhesive for an endoscope, comprising:
   at least one epoxy resin (A) selected from the group consisting of bisphenol A epoxy resins, and phenol novolac epoxy resins;
   a polyamine compound (B); and
   a compound (C) selected from polyethylene glycol diglycidyl ether and polypropylene glycol diglycidyl ether,
   wherein the polyamine compound (B) has, in its molecule, a linear alkylene group or a polyoxyalkylene group, and the number of carbon atoms in the linear alkylene group is 5 to 12, and the average number of repetitions of an oxyalkylene group of the polyoxyalkylene group is 3 to 500.

2. The adhesive for an endoscope according to claim 1, wherein the polyamine compound (B) is a primary polyamine compound.

3. A cured product formed by curing the adhesive for an endoscope according to claim 1.

4. An endoscope comprising the cured product according to claim 3 and a member fixed with the cured product.

5. A method for producing an endoscope, the method comprising fixing a member by using the adhesive for an endoscope according to claim 1.

* * * * *